United States Patent [19]

Hutmacher et al.

[11] Patent Number: 4,766,237
[45] Date of Patent: Aug. 23, 1988

[54] PREPARATION OF 6-AMINOCAPROATES

[75] Inventors: Hans-Martin Hutmacher; Franz J. Broecker, both of Ludwigshafen; Franz Merger, Frankenthal; Rolf Fischer, Heidelberg; Uwe Vagt, Speyer; Heinz-Walter Schneider, Ludwigshafen; Wolfgang Richter, Wachenheim; Wolfgang Harder, Weinheim; Claus-Ulrich Priester, Meckenheim, all of Fed. Rep. of Germany

[73] Assignee: BASF Aktiengesellschaft, Ludwigshafen, Fed. Rep. of Germany

[21] Appl. No.: 7,578

[22] Filed: Jan. 28, 1987

[30] Foreign Application Priority Data

Jan. 28, 1986 [DE] Fed. Rep. of Germany ....... 3602378

[51] Int. Cl.$^4$ ............................................. C07C 67/30
[52] U.S. Cl. .................................... 560/155; 562/553
[58] Field of Search ......................... 560/155; 562/553

[56] References Cited

U.S. PATENT DOCUMENTS 2,777,873  1/1957  Hasek ................................. 560/155
2,956,078  10/1960  Duxbury et al. ................... 560/155

FOREIGN PATENT DOCUMENTS 1132776  11/1968  United Kingdom .

*Primary Examiner*—Werren B. Lone
*Assistant Examiner*—Vera C. Clarke
*Attorney, Agent, or Firm*—Keil & Weinkauf

[57] ABSTRACT

In an improved process for the preparation of 6-aminocaproates by reacting a 5-formylvalerate with ammonia and hydrogen using an alkanol as a solvent in the presence of a hydrogenation catalyst at elevated temperatures and under superatmospheric pressure, the improvement comprises carrying out the reaction at from 40° to 95° C.

10 Claims, No Drawings

PREPARATION OF 6-AMINOCAPROATES

In a process disclosed in German Published Application No. DE-AS 1,050,343, alkyl ω-aminoalkanecarboxylates are prepared by hydrogenating alkyl 5-cyanovalerates at elevated temperatures and under superatmospheric pressure in the presence of ammonia using a nickel or cobalt catalyst. However, the results obtained in this procedure are unsatisfactory since the yield is insufficient for industrial operation.

In another process, disclosed in U.S. Pat. No. 2,777,873, 6-aminocaproates are obtained by reacting 5-formylvalerates with ammonia and hydrogen in the presence of hydrogenation catalysts and alkanols of solvents under superatmospheric pressure and at above 100° C. The results obtained here are unsatisfactory for industrial implementation.

It is an object of the present invention to provide a process for the preparation of 6-aminocaproates from 5-formylvalerates, the said process giving high yields and producing only a small amount of by-products.

We have found that this object is achieved by a process for the preparation of 6-aminocaproates by reacting a 5-formylvalerate with ammonia and hydrogen using an alkanol as a solvent and in the presence of a hydrogenation catalyst at elevated temperatures and under superatmospheric pressure, wherein the reaction is carried out at from 40° to 95° C.

The novel process has the advantage that it gives high yields and only a small amount of by-products are formed. Moreover, the process requires shorter reaction times. The novel process is noteworthy in that high yields are obtained even when methyl 5-formylvalerate is used and methanol is employed as a solvent, although U.S. Pat. No. 2,777,873, column 2, lines 37 to 40, has shown that this is not to be expected and high yields are possible only by using secondary or tertiary esters.

Preferred 5-formylvalerates are alkyl 5-formylvalerates, in particular those of $C_1$-$C_4$-alkanols, such as the methyl, ethyl, propyl, isopropyl or n-butyl ester. Accordingly, suitable starting compounds are methyl 5-formylvalerate, ethyl 5-formylvalerate, propyl 5-formylvalerate, isopropyl 5-formylvalerate and n-butyl 5-formylvalerate. Methyl 5-formylvalerate has become particularly important industrially.

The reaction is carried out in the presence of an alkanol as a solvent. Alkanols which correspond to the alcohol component of the 5-formylvalerate are advantageously used here. Accordingly, preferred solvents are methanol, ethanol, propanol, isopropanol and n-butanol, the combination methyl 5-formylvalerate/methanol being particularly preferred. Advantageously, the 5-formylvalerates are used as a 1-50, advantageously 2-35, in particular 5-25, % strength by weight solution in the stated solvents.

In general, from 2 to 50 moles of ammonia are used per mole of 5-formylvalerate. Particularly good results are obtained when from 5 to 30 moles, in particular from 10 to 25, moles of ammonia are employed per mole of 5-formylvalerate.

The reaction is carried out at from 40° to 95° C., in particular from 60° to 90° C.

From 1 to 20 moles of hydrogen are advantageously used per mole of 5-formylvalerate. It has proven advantageous to maintain a hydrogen partial pressure of from 5 to 1000, preferably from 20 to 500, in particular from 50 to 200, bar.

Preferred hydrogenation catalysts are metals of group VIII of the periodic table, in particular nickel or cobalt catalysts, as well as noble metal catalysts, such as palladium, platinum or rhodium. The catalyst metals can be used in the form of solid catalysts, for example in finely divided form as Raney nickel or Raney cobalt, by the liquid phase procedure or magnetically in the reaction zone, in the form of mixed catalysts or deposited on carriers. Examples of suitable carriers are alumina, silica gel and magnesium silicates. Skeleton catalysts are also suitable. The catalytically active metals are particularly advantageously used in finely divided form. For this reason, skeleton catalysts have proven particularly useful.

Particularly preferably used catalysts are those which are prepared by calcining a compound of the formula $$[(Mg_aNi(II)_bCo(II)_c)Al_2]CO_3(OH)_{16} \times 4H_2O$$

where a is an integer or decimal from 0 to 4 and b and c are each an integer or decimal number from 0 to 6, with the proviso that 2 (a +b +c)=12, at from 200° to 600° C. and then reducing the product with hydrogen at elevated temperatures, eg. from 350° to 450° C. Catalysts obtained by calcining and reducing $$Ni_6Al_2(OH)_{16}CO_3.4H_2O$$

$$Ni_5MgAl_2(OH)_{16}CO_3.4H_2O$$

$$Co_6Al_2(OH)_{16}CO_3.4H_2O$$

$$Co_5MgAl_2(OH)_{16}CO_3.4H_2O$$

have proven particularly useful.

The compounds of the formula I are obtained, for example, as follows: nickel, aluminum, cobalt and magnesium in the form of their water-soluble salts, such as chlorides, sulfates or, preferably, nitrates, are dissolved together in water in a ratio which is very close to the desired composition of the catalyst and in stoichiometry corresponds to formula I.

The total molarity of the metal salt solution in respect of metal ions should be about 0.5-3, preferably 1.0-2. The metal salt solution is heated to 50°-100° C., preferably 80°-100° C., and combined, in the course of from 0.5 to 10, preferably from 1 to 3, minutes, with an equivalent amount or, preferably, a slight excess of a 1-3, preferably 1.5-2.5, molar solution of an alkali metal bicarbonate, the said solution having been heated to 50°-100° C., preferably 80°-100° C. The alkali metal bicarbonate is advantageously used in an excess of up to 20, preferably from 0.5 to 3, % by weight, based on the theoretical amount of bicarbonate. After the addition of the metal salt solution, stirring is advantageously carried out for about 10-30, preferably 15-20, minutes, after which the resulting precipitate is filtered off, washed with water and dried at from 50° to 200° C., preferably from 100° to 160° C. The basic carbonates are obtained in virtually quantitative yields. Particularly suitable alkali metal bicarbonates are sodium bicarbonate and potassium bicarbonate. However, it is also possible to use ammonium bicarbonate for the precipitation. Of course, mixtures of the stated bicarbonates may also be used. Furthermore, it is possible to carry out the precipitation of the metal ions using solutions of alkali metal carbonates, such as sodium carbonate and/or potassium carbonate, if carbon dioxide is passed into the initially taken alkali metal carbonate solution during the precipitation; however, this amounts in the end to precipitation with bicarbonate.

Calcination is advantageously carried out at from 250° to 400° C. for, for example, from 5 to 40, in particular from 15 to 30, hours. Before actually being used, the catalyst is reduced with hydrogen, advantageously at from 180° to 500° C., preferably from 250° to 450° C., in the course of 5 to 100, advantageously from 10 to 25, hours.

Other preferred catalysts are nickel catalysts which contain nickel in finely divided form applied on a carrier, in particular magnesium silicate. Such catalysts advantageously contain nickel in an amount of from 30 to 60% by weight, based on the total catalyst material including the carrier. Catalysts of this type are obtained, for example, by the process described in German Patent No. 1,545,428.

Raney nickel or Raney cobalt is advantageously used as the catalyst, the liquid phase procedure being employed or the catalyst being fixed magnetically to permanent magnets or electromagnetically to soft iron elements.

Furthermore, it is proven advantageous, if, during the reaction, a residence time of from 1 to 20 minutes and a space velocity of from 0.2 to 2.0 kg of 5-formylvalerate per liter of catalyst per hour are maintained.

The reaction can be carried out batchwise, for example in a high pressure vessel, but is preferably carried out continuously, for example in pressure-tight stirred vessels, for example a stirred cascade. It has proven advantageous to avoid back-mixing during the reaction. Tube reactors in which the alcoholic solution of 5-formylvalerate and ammonia are passed over a fixed-bed catalyst have proven particularly useful. The liquid phase procedure has proven particularly suitable here. The 6-aminocaproate is isolated from the reacted mixture in a conventional manner, for example by distillation.

The Examples which follow illustrate the invention.

EXAMPLE 1

An electrically heatable tube reactor having a diameter of 3 cm and a charge height of 71 cm was filled with 500 ml of a nickel oxide/alumina mixed crystal catalyst which had been prepared as described in German Patent 2,024,282, Example 3, calcined with the addition of 2.0% by weight of graphite and then pressed to give pellets of 3 mm diameter. The catalyst was then reduced in a stream of pure hydrogen for 24 hours at 400° C.

Thereafter, 2,200 g/hour of 9.86% strength by weight methanolic methyl 5-formylvalerate solution and 800 ml/hour (488 g/hour) of liquid ammonia were pumped through the reactor from below, while hydrogen was passed through simultaneously, at 80° C. and under 102 bar. The reaction mixture passed from the top of the reactor via a condenser into a separator, from which 2,596 g/hour of product mixture (regulated via the level control) and 207 l/hour of waste gas were removed. According to quantitative gas chromatographic analysis, the discharge of the mixture contained 7.57% of methyl 6-aminocaproate and 0.22% of caprolactam, corresponding to yields of 90.0% of methyl 6-aminocaproate and 3.3% of caprolactam, percentages being based on the completely converted methyl 5-formylvalerate.

EXAMPLE 2

1,176 g/hour of a 19.1% strength methanolic methyl 5-formylvalerate solution and 350 ml/hour (214 g/hour) of liquid ammonia were pumped from below through the reactor described in Example 1, while hydrogen was passed in simultaneously, at 80° C. and under 100 bar. 1,365 g/hour of product mixture and 200 l/hour of waste gas were removed via the separator. According to quantitative gas chromatographic analysis, the discharged mixture contained 13.98% of methyl 6-aminocaproate and 3.0% of caprolactam, the percentages being based on the completely converted methyl 5-formylvalerate.

EXAMPLE 3

A vertical tube reactor having a diameter of 16 mm and a charge height of 25 cm and possessing an oil-heated double jacket was charged with 50 ml of commercial nickel catalyst containing 55% by weight of finely nickel oxide on magnesium silicate (H1-80, in the form of extrudates of 1.5 mm diameter). The catalyst was reduced in the course of 18 hours while increasing the temperature stepwise from 60° to 330° C. and increasing the hydrogen content of the nitrogen/hydrogen mixture used for the reduction from 5 to 50%.

Thereafter, 198.5 g/hour of a 10.0% strength methanolic methyl 5-formylvalerate solution and 46.4 g/hour of liquid ammonia were pumped through the reactor from below, while simultaneously passing through hydrogen, at 80° C. and under 100 bar. The reaction mixture passed from the top of the reactor via a condenser into a separator, from which 243 g/hour of product mixture and 22.6 l/hour of waste gas were removed. According to quantitative gas chromatographic analysis, the reacted mixture contained 7.22% of methyl 6-aminocaproate and 0.15% of caprolactam, corresponding to yields of 87.8% of methyl 6-aminocaproate and 2.4% of caprolactam, percentages being based on the completely converted methyl 5-formylvalerate.

EXAMPLE 4

The Example illustrates the effect of temperature on the hydrogenation yield.

98.9 g/hour of a 10% strength methanolic methyl 5-formylvalerate solution and 20.1 g/hour of liquid ammonia were pumped from below through the reactor described in Example 3, while simultaneously passing in hydrogen, at 100 bar and at different temperatures (10 l/hour of waste gas). Thereafter, ammonia and some of the methanol were removed continuously from the reaction mixtures in a packed column (height 40 cm, diameter 2.5 cm, V$_2$A stainless steel wire mesh rings of 3 mm $\phi$) at 40° C. by stripping with 20 l/h of nitrogen by the countercurrent method, after which 87.7 g/hour of product were discharged in each case.

The table below summarizes the contents of desired product in the discharged mixtures, determined by quantitative gas chromatographic analysis (GC), and the yields calculated from these contents (based on methyl 5-formylvalerate). The experiments a and b are according to the invention, whereas experiment c constitutes a comparison which is not according to the invention.

TABLE

| Temperature [°C.] | GC Values (% by weight) | | Yields [%] | |
|---|---|---|---|---|
| | methyl 6-aminocaproate | Caprolactam | methyl 6-aminocaproate | Caprolactam |
| (a) 60 | 9.51 | 0.12 | 83.7 | 1.4 |
| (b) 80 | 9.78 | 0.33 | 86.1 | 3.5 |
| (c) 120 | 6.85 | 0.97 | 60.3 | 11.0 |

EXAMPLE 5

A rod having a diameter of 9 mm was arranged centrally in a vertical tube reactor having a diameter of 14 mm and a length of 450 mm, permanent magnets having a field strength of 500 Gauss being attached to the said rod. The magnets were laden with 11.0 g of Raney nickel by passing a suspension of Raney nickel in water through the reactor from below.

Thereafter, 773 g/hour of a 12.0% strength by weight methanolic methyl 5-formylvalerate solution and 24 ml/hour of liquid ammonia were pumped through the reactor from below, while 8.7 l/hour of hydrogen were passed through simultaneously, at 76° C. and under 80 bar.

The yield of methyl 6-aminocaproate was 89.1%, based on methyl 5-formylvalerate used. 3.1% of caprolactam, based on methyl 5-formylvalerate, were also obtained.

We claim:

1. A process for producing 6-aminocaproate which comprises: reacting a 5-formylvalerate dissolved in an alkanol with ammonia and hydrogen in the presence of a hydrogenation catalyst under superatmospheric pressure and at a temperature of from 40° to 95° C.

2. The process of claim 1, wherein the catalyst used is prepared by calcining a compound of the formula I $$[(Mg_aNi(II)_bCo(II)_c)Al_2]CO_3(OH)_{16} \times 4H_2O$$

where a is an integer or decimal number from 0 to 4 and b and c are each an integer or decimal number from 0 to 6, with the proviso that $2(a+b+c)=12$, and from 200° to 600° C. and then reducing the product with hydrogen at elevated temperatures.

3. The process of claim 1, wherein a nickel catalyst is used which contains from 30 to 60% by weight of nickel deposited in finely divided form on magnesium silicate.

4. The process of claim 1, wherein the 5-formylvalerate in solution with an alkanol and ammonia is passed over a fixed bed catalyst by the liquid phase method.

5. The process of claim 1, wherein Raney nickel or Raney cobalt is used in suspension.

6. The process of claim 1, wherein Raney nickel or Raney cobalt is fixed magnetically or electromagnetically in the reaction zone.

7. The process of claim 1, wherein a residence time of from 1 to 15 minutes is maintained.

8. The process of claim 1, wherein a space velocity of from 0.2 to 2.0 kg of 5-formylvalerate per liter of catalyst per hour is maintained.

9. The process of claim 1, wherein methyl 5-formylvalerate dissolved in methanol is used.

10. The process of claim 1, wherein the reaction temperature is from 60° to 90° C.

* * * * *